United States Patent
Znaiden et al.

(10) Patent No.: US 6,761,896 B1
(45) Date of Patent: Jul. 13, 2004

(54) SKIN COSMETIC CARE SYSTEM AND METHOD

(75) Inventors: Alexander Paul Znaiden, Trumbull, CT (US); Anthony William Johnson, Fairfield, CT (US); Carol Annette Bosko, Oradell, NJ (US); Samantha Samaras, Long Valley, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/427,868

(22) Filed: Oct. 27, 1999

Related U.S. Application Data

(60) Provisional application No. 60/106,097, filed on Oct. 29, 1998.

(51) Int. Cl.$^7$ .............................. A61K 6/00; A61K 7/00; A61L 15/16; A61F 13/02; A61F 13/00
(52) U.S. Cl. ...................... 424/401; 424/447; 424/448; 424/449; 600/15
(58) Field of Search ............................... 424/447, 448, 424/449, 69, 401; 600/15

(56) References Cited

U.S. PATENT DOCUMENTS

| | | | | |
|---|---|---|---|---|
| 4,489,711 A | * | 12/1984 | Latzke | 600/15 |
| 5,662,925 A | * | 9/1997 | Ebert et al. | 424/447 |
| 5,759,528 A | * | 6/1998 | Yamada et al. | 424/69 |
| 5,817,000 A | * | 10/1998 | Souder | 600/15 |
| 5,965,282 A | * | 10/1999 | Baermann | 428/692 |
| 5,984,856 A | * | 11/1999 | Love | 600/15 |
| 5,993,375 A | * | 11/1999 | Engel | 600/15 |
| 6,024,717 A | * | 2/2000 | Ball et al. | 604/22 |
| 6,068,853 A | * | 5/2000 | Giannos et al. | 424/449 |
| 6,126,588 A | * | 10/2000 | Flamant et al. | 600/15 |
| 6,146,324 A | * | 11/2000 | Engel | 600/15 |

FOREIGN PATENT DOCUMENTS

| | | |
|---|---|---|
| DE | 36 13 280 A1 | 10/1987 |
| DE | 43 25 071 A1 | 1/1995 |

OTHER PUBLICATIONS

Conference abstract by Stanzl, K. "Cosmetic Effects of a Static Magnetic Field on Human Skin", Nov. 1, 1996.
"A Safe, Effective Cellulite Treatment", Happi, Mar. 1996.
Abstract of ES 2099685, Jan. 8, 1995.
BIOflex® Wrinkle–Reducing Face Mask product brochure, 5/95.
BIOflex® Wrinkle–Reducing Face Mask product brochure published more than 1 year prior to the filing date of the present application.
BIOflex® Nature's Alternative product brochure published more than 1 year prior to the filing date of the present application.
Catalogue pictures of magnetic patches published more than 1 year prior to the filing date of the present application.
BIOflex® memo, Sep. 15, 1995.
Pratt et al., "The Effect of the BIOflex® Magnetic Pad on the Flow Rate of 5% Aqueous Saline Solution", International Symposium Biomagnetology, May 29, 1989.
Zablotsky, "Basic Concepts of Bio–Magnetics", Dec. 12, 1995.
BIOflex® "General Information", 1994.
Davis et al., "Magnetic & Magnetic Fields", Firma K.L. Mukhopadhyay, Calcutta, 1970.

* cited by examiner

*Primary Examiner*—Sreeni Padmanabhan
*Assistant Examiner*—Lauren Q Wells
(74) *Attorney, Agent, or Firm*—Ellen Plotkin

(57) ABSTRACT

Cosmetic skin care method based on the application to the skin of a combination of the South pole of a static magnet and a cosmetic composition. Also disclosed is a cosmetic dual patch comprising a static magnet layer and a non-woven, transdermal, hydrogel or silicone sheeting patch carrying a cosmetic benefit ingredient wherein the two layers are adhesively bound to each other.

11 Claims, No Drawings

SKIN COSMETIC CARE SYSTEM AND METHOD

This application claims the benefit of U.S. Provisional Application No. 60/106,097 filed Oct. 29, 1998.

FIELD OF THE INVENTION

The present invention relates to cosmetic skin care system and method comprising a combination of a static magnet and a hydroxy acid.

BACKGROUND OF THE INVENTION

Magnetic fields generated by electric currents have been implicated in a number of disorders including cancer. By contrast, static magnetic fields are considered safe and have been used medicinally for the treatment of pain and for the stimulation of circulation. Static magnets (also known as "permanent magnets") come in different sizes and strength. They may be attached to a human body by straps, belts or tape.

In a cosmetic field, compositions containing magnetized particles, e.g. barium hexaferrite, have been disclosed. The 1996 conference abstract by K. Stanzl discloses that such compositions decrease number of skin folds and increase skin's measured firmness and moisture level. See also Happi, March 1996 article "A Safe Effective Cellulite Treatment" which describes the use of a skin cream containing magnetized barium hexaferrite crystals for reduction of cellulite.

German patent application DE 4325071 (to Lancaster) describes the use of magnetized particles incorporated into a cosmetic base with perflurocarbons in phospholipid vesicles to stimulate blood circulation in the skin and improve hair growth. The composition may be in the form of soap, cream, gel, etc, bandage, plaster or spray. The composition may include anti-oxidants.

It is believed that magnetized particles included in cosmetic compositions have a random orientation.

Spanish patent application ES 2099685 (to Eidos SRL) discloses magnetized cosmetic preparation which contains a magnetic element in the form of a tablet, producing a magnetic field of up to 12,000 Gauss (1.2 Tesla in S.I. units).

German patent application DE 3613280 (to Rhenmagnet Horst Baermann GmbH) discloses a cosmetic face mask containing small permanent magnets (0.5–30 mm). The mask also contains substances which firm or soothe the skin, such as plant or animal extracts. It is said that these substances can penetrate the skin better and their action is improved due to heating and better blood flow resulting from the use of magnets. The magnets may either have two poles or multiple alternating polarity.

Static concentric circular magnets containing alternating poles are marketed by BIOflex for reducing facial wrinkles.

The prior art described above does not disclose any cosmetic skin care method wherein the South pole of a permanent magnet and a cosmetic active are applied to the skin. Likewise, the prior art does not disclose a cosmetic dual patch comprised of a permanent magnet layer and a cosmetic ingredient layer, the latter preferably being a transdermal or a hydrogel patch.

SUMMARY OF THE INVENTION

The invention includes, in its first embodiment (A), a cosmetic method of treating the skin, the method comprising:

(a) applying to the skin the South pole of a static magnet containing at least one North and one South pole; and (b) applying to the skin a cosmetic skin care composition comprising a cosmetic benefit ingredient in a cosmetically acceptable vehicle.

According to the inventive method, the magnet and the composition may be applied concurrently or sequentially.

In its second embodiment (B), the invention also includes a cosmetic dual patch comprising:

(i) a static magnet layer;

(ii) a cosmetic ingredient layer which carries a cosmetic active;

wherein the two layers are attached to each other and the South pole of layer (i) is oriented towards layer (ii).

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

The term "skin" as used herein includes the skin on the face, neck, chest, back, legs, arms, hands and scalp.

Embodiment A: Cosmetic Skin Care Method

The inventive cosmetic skin care method involves application to the skin of the South pole of the permanent magnet. The magnets included in the present invention may have any shape or form. The bar magnets (with one North and one South pole) are preferred. The magnet may be applied to the skin with the help of a strap or a plaster or a tape or an adhesive. Preferably, the thickness of the magnet is at least 1.0 cm, most preferably at least 1.5 cm, in order to maximize the cosmetic benefit attained with the method according to the invention. The typical strength of the magnets suitable for the present invention is in the range of from 0.00004 to 0.2 Tesla, preferably from 0.01 to 0.1 Tesla.

The cosmetic skin care method according to the present invention includes applying to the skin a cosmetic composition containing a cosmetic benefit ingredient. The cosmetic benefit ingredient is preferably selected from hydroxy acids, retinoids, vitamin C, phytic acid and skin depigmenting agents, such as yohimbine and kojic acid.

Hydroxy carboxylic acids enhance proliferation and increase ceramide biosynthesis in keratinocytes, increase epidermal thickness, and increase desquamation of normal skin resulting in smoother, younger looking skin.

The hydroxy acid can be chosen from alpha-hydroxy acids, beta-hydroxyacids (e.g. salicylic acid), other hydroxy-carboxylic acids (e.g., dihydroxycarboxylic acid, hydroxy-dicarboxylic, hydroxytricarboxylic) and mixtures thereof or combination of their stereoisomers (DL, D or L).

Preferably the alpha-hydroxy carboxylic acid is chosen from alpha-hydroxy acids having the general structure (1):

(1)

where M is H or a saturated or an unsaturated, straight or branched hydrocarbon chain containing from 1 to 27 carbon atoms.

Even more preferably the hydroxy carboxylic acid is chosen from lactic acid, 2-hydroxyoctanoic acid, hydroxylauric, glycolic acid, salicylic acid and mixtures thereof. When stereo isomers exist, L-isomer is most preferred.

It is to be understood that depending on the pH of the composition, the hydroxy acid may be present as a salt, e.g., ammonium or potassium or sodium salt.

Certain hydroxy acid esters and especially $C_1$–$C_{30}$ salicylic acid esters have anti-aging and/or oil control activity and may included in the composition. A particularly preferred ester is tridecyl salicylate.

Preferably the amount of the hydroxy acid component present is from 0.01 to 20%, more preferably from 0.05 to 10% and most preferably from 0.1 to 3% by weight.

The cosmetic composition preferably comprises vitamins selected from the group consisting of vitamin A compounds (retinoids) and vitamin C compounds.

Retinoids enhance keratinocyte proliferation in vitro, increase epidermal thickness and increase collagen synthesis by dermal fibroblasts. This results in protection from sun damage and smoothening of wrinkled skin. The term "retinoids" as used herein includes retinoic acid, retinol, retinal and $C_2$–$C_{20}$ retinyl esters. Included in the term "retinoic acid" are 13-cis retinoic acid and all-trans retinoic acid.

The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_2$–$C_{20}$ esters of retinol. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate. Most preferably the ester is selected from $C_2$, $C_3$, and $C_{16}$ esters (because they are more commonly available) or linoleate ester due to its superior efficacy.

A retinoid may be present in the inventive compositions in an amount 33 to 330,000 IU per gram of the composition, preferably 330 to 16,500 IU, most preferably 1,650 to 6,600 IU.

The compositions preferably include kojic acid or yohimbine, as skin depigmenting agents, and/or phytic acid (as an anti-irritant) in an amount of from 0.0001% to 50%, preferably from 0.001% to 25%.

The compositions employed in the inventive method also comprise a cosmetically acceptable vehicle to act as a dilutant, dispersant or carrier for the cosmetic benefit ingredient in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 20 to 70%, optimally between 35 and 60% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxones and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Sunscreens may be present in cosmetic compositions of the present invention. Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

In use, the South pole of the magnet and the composition may be applied sequentially (either the composition or the magnet first) or concurrently to the same skin area. The magnet is applied to the skin for a period of time from minutes to hours. The composition, for example from 1 to 100 ml, is applied to exposed areas of the skin, from a suitable container or applicator and, if necessary, it is then spread over and/or rubbed into the skin using the hand or fingers or a suitable device. The magnet and the composition may be packaged together, as part of the same kit, or may be sold or purchased separately.

Embodiment B: A Cosmetic Dual Patch

In its second embodiment (B), the invention also includes a cosmetic dual patch comprising:
  (i) a static magnet layer;
  (ii) a cosmetic ingredient layer which carries a cosmetic composition comprising a cosmetic benefit ingredient;
wherein the two layers are attached to each other and the South pole of layer (i) is oriented towards layer (ii).

In this embodiment, the magnetic layer may be of any shape or size, but is a thin film. The transdermal or a hydrogel layer carries a cosmetic active as described above for embodiment A. The two layers are attached together with an adhesive system.

The dual patch may be shaped to accommodate the desired area of the application, e.g., as a circle, as a nose strip, as a rectangle. The dual patch may be applied to the skin by means of a tape or an adhesive. The patch is preferably applied to the skin layer (ii) closest to the skin.

The cosmetic benefit ingredient may be any ingredients which benefits the skin, but is preferably selected from the cosmetic benefit ingredients described above for embodiment A.

The following specific examples further illustrate the invention, but the invention is not limited thereto.

Materials and Methods:

The bar magnets used in these studies were obtained from Mc Master Carr, New Brunswick, N.J. These magnets are permanent magnets, also called static magnets (as against electro magnets that create a magnetic field as well as a superimposed electric field) having a North (N) and a South (S) pole. In the experiments described here, where it is mentioned that N or S pole is applied to the cells, it merely means that the N or S pole of the magnet is in closest proximity to the cells, it is impossible to separate one pole from another on any magnet. The magnets used in these studies have a biomagnetic force of 700–750 Gauss at the edges and 280–300 Gauss at the middle of the bar.

The Bioflex Biomagnets used in these studies were obtained from BIOflex Inc., Oakland Park, Fla. The Bioflex magnetic discs are permanent magnets which have concentric circles of alternating N and S poles arranged in circles. This allows for the cells to come in contact with a series of North-South poles. The Bioflex magnets used in these studies have a magnetic field of 240 Gauss at the edge and 87 Gauss in the middle of the magnet.

In all the experiments described here, in order to avoid the variability due to the difference in the magnetic field in different areas of the magnet (edge vs. center), the cells plated in the middle 60 wells of 96 well plates were placed in the middle of the bar or Bioflex magnets. Likewise, the pig skin biopsies were also placed in the middle of the magnets.

The cells used in these studies are normal human keratinocytes and pig skin organ cultures. The normal human keratinocytes isolated from neonatal foreskins by trypsin treatment were growth in DME medium/5% fetal calf serum in the presence of mitomycin C treated 3T3 mouse fibroblasts of establishing dividing colonies. Keratinocytes were grown under these conditions until their third passage. For the experiments, third passage keratinocytes were plated into a serum-free keratincoyte growth medium (KGM; obtained form Clonetics, San Diego, Calif.) containing 0.15 mM calcium. Neonatal human fibroblasts were obtained from Clonetics and grown in Dulbecco's Minimum essential medium (DMEM) containing 10% fetal calf serum. Experiments were conducted in cells between passage numbers 4–10.

Freshly excised 2–3 week old piglet skins were obtained from Buckshire Farms, Pa. The pig skins were washed exhaustively first with soap and then with 10× antibiotic containing medium (penicillin, streptomycin). The pig skins were then dermatomed at 200 microns thickness. Seven (7) mm punch biopsies were made from these washed pig skins. The biopsies are then washed again with the 10× antibiotic medium and finally with normal DMEM (2 washes). Three (3) biopsies were incubated in each transwell plates, epidermal side up, with 1 ml of serum free DMEM fed from the bottom of the plates. Experiments were started 3 days after the biopsies were equilibrated under these conditions.

Effect of Magnetic Force on Keratinocyte Growth:

Keratinocytes were plated in the middle 60 wells of 96 well plates (3000 cells/well). 24 hrs later, the plates were placed on top, in the middle of the magnet (bar or Bioflex) and grown for a further 4 days until the cells become 70–80% confluent. Medium was changed every 2 or 3 days. Control plates were placed on top of a nonmagnetic metal plate and the test plates were placed on top of the bar magnet (North or South side up) or in the middle of the Bioflex magnet. In some studies where the growth of cells were measured as a function of magnetic force, plates were placed on top of one another on top of the magnet such that the bottom plate is closest to the magnet (highest force) and the top plate is the furthest away from the magnet (lowest magnetic force). Studies to assess the effects of North and South magnets were carried out in different incubators to avoid the influence of one magnet on the other. After 4 days of growth, the plates were removed from the incubator, washed 2 times with phosphate buffered saline (PBS), and incubated with 100 ul of a bisbenzimide H 33258 solution (obtained from Calbiochem—stock solution was prepared at 1 mg/ml distilled water,'stored in dark at 4° C. for no longer than 1 week). After 15 min of incubation in the dark at room temperature, fluorescence was measured on a Millipore Cytofluor 2000b (ex/em=360/460 nm). The DNA content was calculated using a standard of calf thymus DNA and expressed as ug/well or as % of control wells which were not exposed to magnets. In all the studies using monolayer cultures mean+/−standard deviation of at least 24 different wells were used to calculate statistical significance using Students t-test.

DNA Synthesis of Pig Skin Organ Cultures:

Three (3) days after equilibrating the pig skin organ cultures prepared as described above, the medium was removed, 1 ml of fresh medium was added, and the wells were treated with different concentrations of lactic acid by adding from a 100 fold concentrated stock in water, directly into the medium. Simultaneous with the addition of lactic acid, selected cultures were also exposed to the South or North pole of a bar magnet or to the Bioflex magnet. The magnets were placed on top of the culture dish to expose the epidermis directly (the organ culture is carried out with the epidermis side on top). Three (3) days later, medium was changed, lactic acid was re-added, and 10 uCi $^3$H-thymidine was added to each well. Plates were incubated for a further 24 hrs. At the end of the incubation period, biopsies were removed, washed in PBS for 1 hr with shaking, and incubated overnight in 10 ml of 2M sodium bromide with shaking to split the epidermis from the dermis. The biopsies were washed with PBS, and the epidermis was peeled off from dermis carefully using a scalpel. The epidermis and dermis were digested with 1 ml of 0.5N NaOH overnight at 50 C, 200 ul was used for counting the radioactivity. The DNA synthesis rate was calculated as cpm/7 mm punch biopsy for dermis or epidermis and in some experiments expressed also as % of controls. All organ culture experiments were conducted with at least 6 replicates, and the mean+/−standard deviation was calculated for statistical analysis using Students t-test.

EXAMPLE 1

Different thickness magnets were compared. The effect of increasing thickness (i.e., increase in magnetic force (Bioflex magnets) on keratinocyte proliferation in keratinocyte monolayer cultures was investigated.

| MAGNET THICKNESS | DNA CONTENT | % OVER CONTROL | P VALUES |
| --- | --- | --- | --- |
| Control (No magnet) | 820 +/− 22 | 0 | |
| 0.75 cm | 825 +/− 45 | 1.73 | |
| 1 cm | 855 +/− 20 | 5.12 | >0.1 |
| 1.5 cm | 930 +/− 28 | 12.4 | >0.05 |

This example evaluated the effects of different thickness BIOflex magnet on keratinocyte proliferation to determine what optimal force is needed for the effects. As seen from the table below, the effect on proliferation was highest as the thickness of the magnet (therefore, the magnetic force) was increased. Magnets of thickness 1.5 cm or higher significantly increased the proliferation of keratinocytes in monolayer cultures.

EXAMPLE 2

The differences between BIOflex magnets (weaker forces, 70–100 gauss) and bar magnets with higher magnetic forces (300–400 gauss) were evaluated. The bar magnet was used with the South pole towards the cells in this study. Magnets increased the proliferation of keratinocytes in 3 separate studies, however bar magnets showed higher increases over the Bioflex magnet in 2 of the 3 studies.

| Groups | Study 1 DNA ug/ well +/− STD (p value) | Study 2 DNA ug/ well +/− STD (p value) | Study 3 DNA ug/ well +/− STD (p value) |
|---|---|---|---|
| Control (no magnet) (48 replicates) | 991 +/− 32.9 (1.0) | 1032 +/− 37.3 (1.0) | 1085 +/− 38.5 (1.0) |
| Bioflex magnet (48 replicates) | 1048 +/− 32.3 ($p > .0001$) | 1073 +/− 43 ($p > .0001$) | 1179 +/− 46.4 ($p > .0001$) |
| Bar magnet (south pole) (24 replicates) | 1075 +/− 43.6 ($p > .0001$) | 1092 +/− 47 (p..0001) | 1176 +/− 56.8 ($p > .0001$) |

EXAMPLE 3

Example 3 evaluated the synergy between lactic acid and magnetic field in inducing the proliferation of keratinocytes. In this study, using in vitro keratinocyte cultures, 2 mM lactic acid increased proliferation by 5.4%. This increase was not statistically significant. Bioflex magnet alone also stimulated proliferation by 5.5%, which was also not statistically significant, under the conditions used for the experiment. However, lactic acid in the presence of the BIOflex magnet stimulated keratincoyte proliferation by 15%, which was statistically significant ($p > 0.001$). Therefore, this experiment revealed a synergy between lactic acid and magnetic force in the stimulation of keratinocyte proliferation.

Synergy between lactic acid and magnetic field on keratinocyte proliferation as measured by DNA content:

|  | CONTROL (NO MAGNET) | LACTIC ACID (2 MM) | BIOFLEX MAGNET | LACTIC ACID + BIOFLEX MAGNET |
|---|---|---|---|---|
| Average | 241 | 254 | 256 | 277 |
| Standard deviation |  | 5.3 | 6.3 | 15 |
| p value |  | .35 | .36 | 0.001 |

EXAMPLE 4

Example 4 compared the magnet geometry (north vs. south; bar magnet vs. BIOflex circular magnet) on epidermal cell proliferation of pig skin organ culture. Culture of pig skins were carried out as described in the methods. Bioflex magnet had no significant effect on epidermal proliferation in this experiment. Bar magnet (both North and South) showed higher stimulation of proliferation. Effect of North pole of bar magnet was minimal (24% over control) and was not statistically significant. However, South pole of bar magnet significantly stimulated proliferation (87% over control) of pig epidermal cells. This study suggests that bar magnet is better than BIOflex magnet (due to higher magnetic field) and the south pole of bar magnet is significantly better than the north pole.

Comparison of different magnet geometry on epidermal proliferation in organ culture.

| MAGNET GEOMETRY | DNA SYNTHESIS +/− STD (CPM/7MM BIOPSY) | % OF CONTROL | P VALUE |
|---|---|---|---|
| Control (no magnet) | 4346 +/− 291 | 100 | 1 |
| Bioflex circular | 4427 +/− 310 | 102 | 0.75 |
| Bar magnet South | 8125 +/− 809 | 187 | 0.001 |
| Bar magnet North | 5411 +/− 1073 | 124 | 0.172 |

EXAMPLE 5

Example 5 evaluated the lactic acid (LA) dose response and the synergy between lactic acid and the south pole of bar magnet on pig epidermal cell proliferation. Lactic acid effect was significant only at 2.0 mM, lower levels 0.02 and 0.2 mM had no significant effect on epidermal proliferation in this experiment. As seen before, south pole of the bar magnet had significant influence on proliferation. As one would expect, South pole magnet in the presence of different concentrations of lactic acid were all significantly higher proliferation compared to controls. When compared to south pole magnet alone, only the highest lactic acid was significantly different (similar to the finding that only the highest lactic acid was significant). Synergies were observed with LA and South pole (2 mM LA alone was 43% over control; south pole alone was 87% over control; LA+South pole was 165% over control which is more than the additive response 43+87=130).

|  | DNA SYNTHESIS (CPM/BIOPSY) MEAN +/− STD | AS % OF CONTROL | P VALUE VS. CONTROL | P VALUE VS. SOUTH POLE MAGNET |
|---|---|---|---|---|
| Control (no magnet, no Lactic acid, LA)) | 4346 +/− 291 | 100 | 1 |  |
| 0.02 mM LA | 4670 +/− 497 | 107 | 0.37 |  |
| 0.2 mM LA | 5030 +/− 958 | 115 | 0.30 |  |
| 2.0 mM LA | 6216 +/− 1035 | 143 | 0.04 |  |
| South Pole Magnet alone | 8125 +/− 809 | 187 | 0.001 | 1.00 |
| South + 0.02 mM LA | 7915 +/− 2807 | 182 | 0.01 | 0.90 |
| South + 0.2 mM LA | 8402 +/− 512 | 193 | 0.001 | 0.64 |
| South + 2.0 mM LA | 11523 +/− 2123 | 265 | 0.001 | 0.06 |

EXAMPLE 6

Example 6 illustrates the comparison between south and north pole magnet for its synergy with lactic acid in pig skin epidermal proliferation. South pole exposed skin showed higher proliferation rate than the skins exposed to north pole. 0.2 mM Lactic acid alone had no significant effect on epidermal proliferation (similar data to that in example 5). However, when combined with north or south pole magnet, 0.2 mM lactic acid showed significantly higher proliferation rate compared to control. South+LA group showed the maximal proliferative response (146% over control) and this was synergistic when compared to LA alone or South pole alone control. North+LA group showed 112% over control proliferative response, but this was not synergistic when compared to north alone control. Thus, this experiment confirms the previous finding that lactic acid+south pole magnet show synergistic growth response of epidermal cells in pig skin organ cultures.

There are four constructions as detailed below:

8A. Nonwoven Patch
  A. magnetic sheet (South side down)
  B. Adhesive layer
  C. Nonwoven impregnated w/adhesive and active
  (Optional) D. Adhesive layer Example: hydroxy acid is combined with excipients and a water-soluble adhesive and impregnated into the nonwoven. An example of an adhesive/active composition is:
  80% of an anionic polymer such as Gantrez S-97
  2% amino-methyl-propanol
  6% lactic acid
  0.2% preservative
  qs water Layer B attaches Layer A to Layer C and is an adhesive selected from Table 1 which is compatible with Layers A and C.

| GROUPS | DNA SYNTHESIS (CPM/BIOPSY) MEAN +/− STD | AS % OF CONTROL | P VALUE VS. CONTROL | P VALUE NORTH VS. SOUTH | P VALUE SOUTH VS. SOUTH + LA | P VALUE NORTH VS. NORTH + LA |
|---|---|---|---|---|---|---|
| Control (no magnet, no LA) | 32958 +/− 11944 | 100 | 1.00 | | | |
| South Pole | 60668 +/− 23675 | 184 | .0063 | 1.00 | 1.00 | |
| North Pole | 54831 +/− 12393 | 166 | .0045 | .59 | | 1.00 |
| Control + 0.2 mM LA | 41076 +/− 24767 | 124 | .407 | | | |
| South + LA | 81393 +/− 11738 | 246 | >.0001 | | .07 | |
| North + LA | 69726 +/− 29913 | 211 | .0091 | | | .306 |

EXAMPLE 7

In example 7, dermal proliferation was measured as a function of lactic acid and magnetic pole treatment. As with the epidermis, south pole showed bigger increase than the north pole. Lactic acid alone had a significant stimulation of dermal proliferation. However, in contrast to the findings in the epidermis, combinations of magnet with lactic acid showed no synergy in the dermis.

Layer C is a nonwoven impregnated with an active and a water-soluble adhesive to attach it to skin. The adhesive is selected from Table 2. In one alternative form of the product the adhesive in Layer C is used to adhere Layer C to Layer A.

Another alternative form is where Layer D, a pressure sensitive adhesive (PSA), is applied to the nonwoven. The PSA is applied as a continuous layer or as a continuous layer which is semi-permeable to water and the active.

| GROUPS | DNA SYNTHESIS (CPM/BIOPSY) MEAN +/− STD | AS % OF CONTROL | P VALUE VS. CONTROL | P VALUE NORTH VS. SOUTH | P VALUE SOUTH VS. SOUTH + LA | P VALUE NORTH VS. NORTH + LA |
|---|---|---|---|---|---|---|
| Control (no magnet, no LA) | 9435 +/− 2221 | 100 | 1.00 | | | |
| South Pole | 13490 +/− 7673 | 142 | .234 | 1.00 | 1.00 | |
| North Pole | 11839 +/− 4095 | 125 | .235 | .639 | | 1.00 |
| Control + 0.2 mM LA | 15306 +/− 4656 | 162 | .019 | | | |
| South + LA | 17244 +/− 4259 | 182 | .0025 | | .298 | |
| North + LA | 16886 +/− 2227 | 178 | .0021 | | | .092 |

EXAMPLE 8

Patches are constructed to provide for a South-oriented magnetic layer attached to an active-containing substrate layer for application to skin such that the active migrates from its layer to the skin within the oriented magnetic field.

8B. Hydrogel Patch
  A. Magnetic sheet (South side down)
  B. Adhesive layer
  C. Nonwoven impregnated w/hydrogel and a hydroxy acid
  (Optional) D. Adhesive layer Example: a polyester nonwoven with an impregnated gel in 1:10 ratio. An example of a gel composition is:

55% water

28% Na sale of polyacrylate derivative

15% glycerin

1% xanthan gum

1% NaCl

Layer B attaches Layer A to Layer C and is an adhesive selected from Table 1 which is compatible with Layers A and C.

The adhesion of Layer C to the skin is achieved by the surface tension of the gel.

An alternate form is where Layer D, a pressure sensitive adhesive (PSA), is applied to the nonwoven. The PSA is applied as a non-continuous layer or as a continuous layer which is semi-permeable to water and the active.

8C. Pressure Sensitive Adhesive (PSA) Patch

A. Simple Example: Adhesive with Glycolic Acid

A. Magnetic sheet (South side down)

(Optional) B. Adhesive layer (Optional) F. Plastic film

C. Adhesive layer with active mixed in example: 5% glycolic acid

Example of Liquid Reservoir:

5% glycerol

4% succinic acid

2% glycolic acid

1% Carbopol 0.2% preservative qs water

B. Controlled Release

A. Magnetic sheet (South side down)

B. Adhesive layer

F. Plastic film

C1. Liquid reservoir with 2% lactic acid

C2. Semi-permeable membrane (rate-controlling)

D. Adhesive layer

Example of Liquid Reservoir:

5% glycerol

4% succinic acid

2% glycolic acid

1% Carbopol 0.2% preservative qs water

In the simple patch, the adhesive in Layer C, selected from Table 1, may be adequate to attach it to Layer A. If not, Layers B and F may be added. Layer B is an adhesive selected from Table 1 which is compatible with Layers A and C. Layer F is a plastic film constructed of polyurethane, polyester, polyethylene or polyvinyl chloride. Film thickness can range from 1.0 ml to 10.0 mils. Film can also be a foam, with a thickness between 20–200 mils.

The controlled release patch uses Layers B and F to separate and contain the reservoir containing a liquid plus active(s) from the magnetic sheet. The adhesive Layer D may be a non-continuous layer applied to the semi-permeable membrane or as a continuous layer which does not significantly affect the flow of water and the active(s).

8D. Silicone Sheet Patch

| A. Magnetic sheet (South side down) | A. Magnetic sheet (South side down) |
|---|---|
| B. Adhesive layer | B. Adhesive layer |
| C. Pliable silicone sheet with a hydroxy acid | C. Pliable pouch containing silicone fluid or gel with a hydroxy acid |

Layer B attaches Layer A to Layer C and is an adhesive selected from Table 1 which is compatible with Layers A and C.

The Silicone sheet is of the type suitable for the treatment of scars, wounds, stretch marks and/or other cutaneous conditions. The silicone fluid or gel in the pouch is likewise of the type useful for treating cutaneous conditions.

TABLE 1

Classes of Adhesives

| acrylic | vinyl acrylic | acrylate | styrene butadiene |
|---|---|---|---|
| epoxy | chloropane | elastomer | polyvinyl alcohol |
| polyimdie | silicone | urethane | polyvinyl acetate |
| ethylene vinylacetate | | natural or snythetic rubber | |

TABLE 2

Classes of Water-Soluble Adhesives

| acrylic | acrylate | vinyl acrylic | alkyl vinyl acetate |
|---|---|---|---|
| sytrene sulfonate | | betaine | polyvinyl alcohol |
| N-vinyl cyclic amides | | succinate | styrene |
| alkyl vinyl ether | | vinyl pyridine | maleate |

EXAMPLE 9

Phytic acid (0.5%) was examined for its effect on cytokine release by MelanoDerm Living Skin Equivalents in the presence and absence of South Pole magnetism. After 24 hours incubation, during which one set of tissues was exposed to South Pole magnetism and an equivalent duplicate series was not, the culture medium was assayed for IL1-a and PGE-2. In the absence of magnetism there was a significant increase in medium concentration of both IL1-a and PGE-2. These increases were suppressed in the presence of South pole magnetism.

Materials

Living Skin Equivalent: MelanoDerm™ MEL-300, a 3-dimensional epidermal model containing functioning melanoctyes produced by MatTek Corporation, Ashland, Mass., was the tissue used for this experiment.

Phytic Acid

Phytic acid was tested at a concentration of 0.5% in water. This concentration was shown to be non-toxic to MelanoDerm tissue (no effect on tissue viability as assessed by MTT) in a preliminary experiment.

Magnet: 6 inch×4 inch×1 inch Rectangular permanent orientated Ferrimag Ceramic magnet (3.4 megagauss oersteds) from Edmund Scientific Co. providing a field strength approximately 650+/−200 gauss at incubation plate level above the magnet surface.

Methods

In Vitro Incubation:

Fifty (50) microliters of phytic acid solution (0.5%) was applied to the stratum corneum surface of 4 MEL-300 tissues. Eight (8) untreated MEL-300 tisues served as controls. Half the tissues (i.e. 2 phytic acid and 4 untreated controls) were placed on the 6 inch×4 inch South Pole surface of the Ferrimag magnet for 24 hours incubation (37 degrees centigrade; 5% $CO_2$).

After the 24 hr incubation the tissues were removed from the incubation medium and assayed for MTT to confirm tissue viability. The incubation medium was assayed for content of cytokines IL1-a and PGE-2. The tissue samples were refrigerated and a second determination of cyotkines was made 7 days later. The cytokine assays were performed using commercially available 96 well Elisa kits.

Results

Elisa results for IL1-a and PGE-2 are summarized in Table I and detailed in Table II.

TABLE I

Effect of magnetism on Phytic acid stimulation of cytokine release

| | IL1-a release % Untreated | PGE-2 release % Untreated |
|---|---|---|
| Phytic acid No Magnetism | 99% | 191% |
| Phytic acid + Magnetism | 16% | −2% |
| P value | 0.057 | 0.002 |

These results demonstrate that magnetism suppresses phytic acid stimulation of IL1-a and PGE-2 from skin epidermal tissue. As both IL1-a and PGE-2 are pro-inflammatory mediators, the suppression off their release by magnetism is indicative of an anti-inflammatory effect of magnetism. As the magnet has no significant effect on cytokine release in the absence of active, the results indicate an anti-inflammatory effect of magnetism on the action of actives like phytic acid which stimulate skin production of inflammatory mediators.

It can be seen from the results in Tables I and II that the South Pole magnetism inhibits the pro-inflammatory action of phytic acid on skin epidermal tissue.

EXAMPLE 10

Kojic acid, Vitamin C, and Yohimbine were examined for their ability to reduce pigmentation in the MelanoDerm Living Skin Equivalent in the presence and absence of South Pole magnetism. After 14 days of incubation, during which one series of tissues was exposed to South Pole magnetism and an equivalent duplicate series was not, the melanin color formed in each tissue was estimated using primary color image analysis.

The results show a reduction in pigmentation by each of the actives in the absence of magnetism and an enhanced reduction of pigmentation in the presence of South pole magnetism.

Materials

Living Skin Equivalent:

MelanoDerm™ MEL-300, a 3-dimensional epidermal model containing functioning melanoctyes produced by MatTek Corporation, Ashland, Mass., was the tissue used for this experiment. Each MEL-300 kit has 24 tissue pieces.

Depigmenting Actives:

Three depigmenting actives were added to the Melanoderm incubation medium at the following final concentrations, (a) Kojic acid—500 micro-molar (b) Yohimbine—25 micro-molar (c) Ascorbic acid—285 micro-molar Magnet:

6 inch×4 inch×1 inch Rectangular permanent orientated Ferrimag Ceramic magnet (3.4 megagauss oersteds) from Edmund Scientific Co. providing a field strength approximately 650+/−200 gauss at incubation plate level above the magnet surface.

Methods

In Vitro Incubation:

Two (2) MEL-300 kits, each with 24 tissue pieces, were prepared with identical application of actives. Each active, Vitamin C, Kojic acid & Yohimbine, was applied to the incubation medium of 5 tissues at the concentrations specified above. 4 tissues were untreated. (The remaining 5

TABLE II

Effect of Phytic acid on tissue release of IL1-a and PGE-2

| | IL1-a(i) | IL1-a(ii) | T-Test vs untreated | Paired t-Test Mag vs No Mag. p (T <= t)2-Tail | PGE-2(i) | PGE-2 (ii) | T-Test vs untreated | Paired t-Test Mag vs No Mag. p (T <= t)2-Tail |
|---|---|---|---|---|---|---|---|---|
| Untreated | 107.8 | 90.7 | | | 2540 | 1520 | | |
| | 116.4 | 117.1 | | | 3138 | 2104 | | |
| | 172.4 | 83.7 | | | 2069 | 910 | | |
| | | 47.2 | | | 1460 | 396 | | |
| Mean Untreated | | 105 +/− 38 | | | | 1767 +/− 882 | | |
| plus Magnet | 126.1 | 63.5 | | | 950 | 228 | | |
| | 163.7 | 89.1 | | | 1793 | 646 | | |
| | 235.8 | 120.2 | | | 3736 | 2583 | | |
| | | 113.2 | | | 4204 | 3021 | | |
| Mean | | 130 +/− 56 | 0.345 | | | 2145 +/− 147 | 0.544 | |
| Phytic/No magnet | 285.3 | 186.2 | | | 5326 | 5621 | | |
| | 222.9 | 141.1 | | | 4673 | 4923 | | |
| Mean | | 209 +/− 61 | 0.0007 | | | 5136 +/− 421 | 0.001 | |
| Phytic/Magnet | 239.1 | 158.2 | | | 2056 | 1899 | | |
| | 108.9 | 98.4 | | | 2387 | 2030 | | |
| Mean | | 151.2 +/− 64 | 0.164 | 0.057 | | 2093 +/− 208 | 0.493 | 0.002 | tissues were treated with a melanin stimulating active not reported here because it had no significant effect on pigmentation). One Mel-300 kit prepared as above was placed on the 6 inch×4 inch South Pole surface of the Ferrimag magnet for incubation, and the identical second Mel-300 kit was incubated at the opposite side (top left vs bottom right) of the same incubator and additionally shielded from the magnet.

The tissues were incubated for 14 days in maintenance medium at 37 degrees centigrade and a constant atmosphere (5%$CO_2$). The maintenance medium and actives were replenished 4 times weekly. At 7 days, 2 tissues were removed from each active and control group leaving 3 tissues in each group (2 in the untreated group) for day 14 evaluation.

Assessment of Melanin Pigment Production:

At the day 14 completion of the experiment the tissue pieces of each Mel-300 incubation plate were photographed from above. Each tissue appeared as a small disc varying in brown color intensity. The photographs of two Mel-300 incubation plates (one incubated on the magnet and one without magnetism) were scanned into a Pentium II computer and the color primary color content of each disc was measured using a color analysis macro within an Optimas image quantification software package. The blue color content was used as an index of melanin pigment (preliminary experiments confirmed that the principle primary color of melanin is blue using this image analysis system—this was established by comparing brown freckles and age spots with surrounding non-pigmented skin in color photographs of Caucasian human skin). The blue color intensity scale is 0–255 where 0 is saturation with blue color and 255 is total absence of blue color. The actual blue scale reading of each tissue sample was converted to a % blue value by computing it's proportion of the full range of 0to 255.

The key findings are presented in Table below.

Effect of Magnetism on the Activity of Depigmenting Actives

| Depigmenting Active | Pigmentation Reduction % No Magnet (A) | Pigmentation Reduction Magnet % South Pole (B) | A-B | Mean A-B |
|---|---|---|---|---|
| Kojic Acid | −4.77 | −9.21 | −4.4 | |
| | −8.72 | −10.02 | −1.3 | |
| | −4.27 | 4.75 | −0.48 | |
| | | Mean Difference | | −2.06 |
| Yohimbine | −5.63 | −8.08 | −2.45 | |
| | −3.8 | −6.76 | −2.96 | |
| | 1.85 | −2.55 | −4.4 | |
| | | Mean Difference | | −3.27 |
| Vitamine C | −4.21 | −6.18 | −1.97 | |
| | −2.65 | −6.34 | −3.69 | |
| | 1.7 | −4.55 | −6.25 | |
| | | Mean Difference | | −3.97 |
| | t-test A vs. B = | 0.038056 | | |

In the absence of magnetism, the 3 depigmenting actives show less pigmentation than the untreated control tissue. The tissues incubated on the South Pole side of the magnet show a greater reduction in pigmentation relative to untreated control than seen without the magnet. The difference between the actives in the presence and absence of magnetism is statistically significant (p<0.05). The pigmentation seen in control tissues was not significantly different for no magnet (78%) and magnet (79%), demonstrating that in the absence of actives, South pole magnetism does not have a depigmenting effect. Thus, the results demonstrate that South pole magnetism enhances the skin depigmenting action of Kojic acid, Yohimbine and Vitamin C.

EXAMPLE 11

This example measured the effect of various actives in combination with magnets on lipid production by sebocytes in vitro.

Secondary cultures of human sebocytes obtained from an adult male were grown in the inner 24 wells of 48-well tissue culture plates (Costar Corp.; Cambridge, Mass.) until confluent. Sebocyte growth medium consisted of Clonetics Keratinocyte Basal Medium (KBM) supplemented with 14 ug/ml bovine pituitary extract, 0.4 ug/ml hydrocortisone, 5 ug/ml insulin, 10 ng/ml epidermal growth factor, $1.2 \times 10^{-10}$ M cholera toxin, 100 units/ml penicillin, and 100 ug/ml streptomycin. All cultures were incubated at 37° C. in the presence of 7.5% $CO_2$. Medium was changed three times per week.

On the first day of experimentation, the growth medium was removed and the sebocytes washed three times with sterile Dulbecco's Modified Eagle Medium (DMEM; phenol red free). Fresh DMEM was added to each sample (triplicates) with 5 microliter of test agent solubilized in ethanol (312.5 uM iso-tridecylsalicylate or 10 uM Retinyl Linoleate; 6 replicates for each sample). Controls consisted of addition of ethanol alone. Each magnet was sandwiched between 2 plates for 24 hours. For 2 of the sebocyte plates, the configuration was North magnet pointing up, for 2 other plates, the configuration was reversed (South magnet up), and one plate served as a control (no presence of magnets).

After 24 hours, addition of $^{14}$C-acetate buffer (5 mM final concentration, 56 mCi/mmol specific activity) was performed. Sebocytes were then returned to the incubator for four hours after which each culture was rinsed three times with phosphate buffered saline to remove unbound label. Radioactive label remaining in the sebocytes was harvested and counted using a Beckman scintillation counter.

Statistical Analysis was performed using JMP software package.

| Treatment | DPMs (AVG) | DPMs (STD DEV) | % Reduction |
|---|---|---|---|
| Plate A: No Magnet Presence | 4569.6 | 258.8 | |
| 312.5 uM TDS | 2913.0 | 196.0 | 36.3 |
| 10 uM Retinyl Linoleate | 4198.1 | 736.5 | 3.9 |
| Plate B: North Magnet Up (Top Plate) | 4409.7 | 687.2 | |
| 312.5 uM TDS | 3367.8 | 718.3 | 23.6 |
| 10 uM Retinyl Linoleate | 4123.0 | 580.2 | 6.5 |
| Plate C: North Magnet Up (Bottom Plate) | 3726.4 | 801.7 | |
| 312.5 uM TDS | 3543.9 | 773.8 | 4.9 |
| 10 uM Retinyl Linoleate | 3660.1 | 986.4 | 1.8 |
| Plate D: South Magnet Up (Top Plate) | 3563.6 | 384.7 | |
| 312.5 uM TDS | 3040.0 | 457.9 | 14.7 |
| 10 uM Retinyl Linoleate | 3619.4 | 461.6 | −1.6 |
| Plate E: South Magnet Up (Bottom Plate) | 3369.2 | 635.4 | |
| 312.5 uM TDS | 2677.4 | 348.0 | 20.5 |
| 10 uM Retinyl Linoleate | 3181.1 | 523.1 | 5.6 |

|  | Cont | Cont NT | RL NT | RL | Cont NB | RL NB | RL ST | Cont ST | TDS NB | Cont SB | TDS NT | TDS ST | RL SB | TDS |
|---|---|---|---|---|---|---|---|---|---|---|---|---|---|---|
| Cont | −712.4 | −553.8 | −429.4 | −342.2 | 129.5 | 195.8 | 236.5 | 292.3 | 329.9 | 486.7 | 488.1 | 815.9 | 898.9 | 942.9 |
| Cont-NT | −553.8 | −712.4 | −588.0 | −500.8 | −29.1 | 37.2 | 77.9 | 133.7 | 171.3 | 328.1 | 329.5 | 657.3 | 740.2 | 784.3 |
| RL-NT | −429.4 | −588.0 | −659.6 | −573.4 | −101.7 | −35.4 | 5.3 | 61.2 | 98.7 | 255.5 | 256.9 | 584.8 | 667.7 | 711.7 |
| RL | −342.2 | −500.8 | −573.4 | −712.4 | −240.7 | −174.4 | −133.7 | −77.9 | −40.3 | 116.5 | 117.9 | 445.7 | 528.6 | 572.7 |
| Cont-NB | 129.5 | −29.1 | −101.7 | −240.7 | −712.4 | −646.1 | −605.4 | −549.6 | −512.0 | −355.2 | −353.8 | −25.9 | 56.9 | 100.9 |
| RL-NB | 195.8 | 37.2 | −35.4 | −174.4 | −646.1 | −712.4 | −671.7 | −615.9 | −578.3 | −421.5 | −420.1 | −92.2 | −9.4 | 34.7 |
| RL-ST | 236.5 | 77.9 | 5.3 | −133.7 | −605.4 | −671.7 | −712.4 | −656.6 | −619.0 | −462.2 | −460.8 | −132.9 | −50.0 | −6.0 |
| Cont-ST | 292.3 | 133.7 | 61.2 | −77.9 | −549.6 | −615.9 | −656.6 | −712.4 | −674.9 | −518.0 | −516.6 | −188.8 | −105.9 | −61.9 |
| TDS-NB | 329.9 | 171.3 | 98.7 | −40.3 | −512.0 | −578.3 | −619.0 | −674.9 | −712.4 | −555.6 | −554.2 | −226.3 | −143.4 | −99.4 |
| Cont-SB | 486.7 | 328.1 | 255.5 | 116.5 | −355.2 | −421.5 | −462.2 | −518.0 | −555.6 | −712.4 | −710.9 | −383.2 | −300.3 | −256.2 |
| TDS-NT | 488.1 | 329.5 | 256.9 | 117.9 | −353.8 | −420.1 | −460.8 | −516.6 | −554.2 | −710.9 | −712.4 | −384.6 | −301.7 | −257.7 |
| TDS-ST | 815.9 | 657.3 | 584.8 | 445.7 | −25.9 | −92.3 | −132.9 | −188.8 | −226.3 | −383.2 | −384.6 | −712.4 | −629.5 | −585.5 |
| RL-SB | 898.9 | 740.2 | 667.7 | 528.6 | 56.9 | −9.4 | −50.0 | −105.9 | −143.4 | −300.3 | −301.7 | −629.5 | −712.4 | −668.4 |
| TDS | 942.9 | 784.3 | 711.7 | 572.7 | 100.9 | 34.7 | −6.0 | −61.9 | −99.4 | −256.2 | −257.7 | −585.5 | −668.4 | −712.4 |
| TDS-SB | 1143.7 | 985.1 | 911.3 | 773.5 | 301.8 | 235.5 | 194.8 | 138.9 | 101.4 | −55.4 | −56.8 | −384.6 | −467.6 | −511.6 |

Comparisons for each pair using Student's T-Test
Alpha = 0.05
Positive Values Show Pairs of Means that are Significantly Different
Abbreviations:
Cont: Control Plate with No Magnets
TDS: iso-tridecylsalicylate
RL: Retinyl Linoleate
NT: North Magnet Facing Up, Tissue Culture Plate Above Magnet
NB: North Magnet Facing Up, Tissue Culture Plate Below Magnet
ST: South Magnet Facing Up, Tissue Culture Plate Above Magnet
SB: South Magnet Facing Up, Tissue Culture Plate Below Magnet It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic dual patch comprising:
   (i) a static magnet layer with North and South Poles;
   (ii) a nonwoven, transdermal, hydrogel or silicone sheeting patch carrying a cosmetic benefit ingredient;
   wherein the two layers are adhesively bound to each other and the South Poles of layer (i) are oriented towards the patch layer (ii).

2. A cosmetic method of treating the skin, the method comprising:
   (a) applying to the skin the South pole of a static magnet; and
   (b) applying to the skin a cosmetic skin care composition comprising a cosmetic benefit ingredient in a cosmetically acceptable vehicle.

3. The method of claim 2, wherein the thickness of the magnet is at least 1 cm.

4. The method of claim 2 wherein the cosmetic benefit ingredient is selected from the group consisting of alpha- or beta-hydroxycarboxylic acid, retinoids, Vitamin C, phytic acid, yohimbine and kojic acid.

5. The cosmetic dual patch according to claim 1 wherein the cosmetic benefit ingredient is selected from the group consisting of alpha- or beta-hydroxycarboxylic acid, retinoids, Vitamin C, phytic acid, yohimbine and kojic acid.

6. The cosmetic dual patch according to claim 5 wherein the hydroxycarboxylic acid is in a form selected from the group consisting of a free acid, a salt, an ester and mixtures thereof.

7. The cosmetic dual patch according to claim 6 wherein the hydroxycarboxylic acid is selected from a group consisting of lactic acid, 2-hydroxyoctanoic acid, hydroxylauric acid, glycolic acid, salicylic acid and mixtures thereof.

8. The cosmetic dual patch according to claim 5 wherein the retinoids are selected from the group consisting of retinol, a $C_2$–$C_{20}$ ester of retinol, retinoic acid and combinations thereof.

9. The method according to claim 4 wherein the hydroxycarboxylic acid is in a form selected from the group consisting of a free acid, a salt, an ester and mixtures thereof.

10. The method according to claim 4 wherein the hydroxycarboxylic acid is selected from a group consisting of lactic acid, 2-hydroxyoctanoic acid, hydroxylauric acid, glycolic acid, salicylic acid and mixtures thereof.

11. The method according to claim 4 wherein the retinoids are selected from the group consisting of retinol, a $C_2$–$C_{20}$ ester of retinol, retinoic acid and combinations thereof.

* * * * *